United States Patent [19]

Akira et al.

[11] 4,337,778
[45] Jul. 6, 1982

[54] BLOOD PRESSURE MEASURING APPARATUS

[75] Inventors: Abe Akira, Takatsuki; Shoji Kimura, Kameoka; Miyawaki Yoshinori, Yawata, all of Japan

[73] Assignee: Omron Tateisi Electronics, Inc., Kyoto, Japan

[21] Appl. No.: 169,202

[22] Filed: Jul. 15, 1980

[30] Foreign Application Priority Data

Aug. 1, 1979 [JP] Japan .................................. 54/98843

[51] Int. Cl.³ ............................................. A61B 5/02
[52] U.S. Cl. .................................................. 128/680
[58] Field of Search ............................... 128/680–681, 128/686

[56] References Cited

U.S. PATENT DOCUMENTS

| | | | |
|---|---|---|---|
| 3,056,401 | 10/1962 | Greenspan et al. | 128/681 |
| 3,148,677 | 9/1964 | Smith | 128/680 |
| 3,480,005 | 11/1969 | Edwards | 128/680 |
| 3,878,834 | 4/1975 | Sanderson | 128/680 |
| 3,905,354 | 9/1975 | Lichowsky | 128/681 |
| 3,906,939 | 9/1975 | Aronson | 128/680 |
| 3,920,004 | 11/1975 | Nakayama | 128/680 |
| 4,033,337 | 7/1977 | Raczkowski | 128/686 |
| 4,175,547 | 11/1979 | Kurihara | 128/680 |

*Primary Examiner*—Lee S. Cohen
*Assistant Examiner*—Francis J. Jaworski
*Attorney, Agent, or Firm*—Wegner & Bretschneider

[57] ABSTRACT

Blood pressure measuring apparatus comprising an occluding cuff including an inflatable bladder, an air guiding passage one end of which is connected to the bladder, an air pressure control connected to the other end of the passage for inflating or deflating the bladder through the passage, a microphone within said passage for sensing Korotkoff sounds which are propagated through the passage from the bladder and for generating Korotkoff sound signals, a pressure transducer for sensing the pressure within the bladder and for generating pressure signals, and a circuit operative in response to the Korotkoff sound and pressure signals to measure the systolic and diastolic blood pressures of a patient whose blood pressure is to be measured.

11 Claims, 7 Drawing Figures

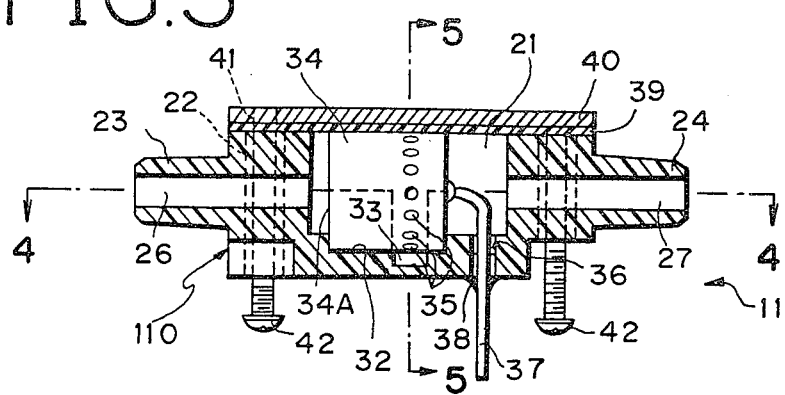
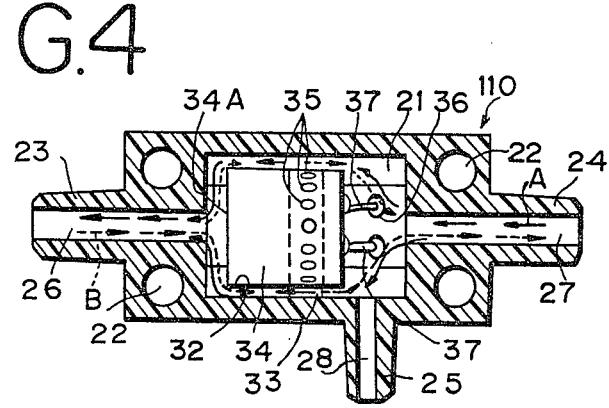
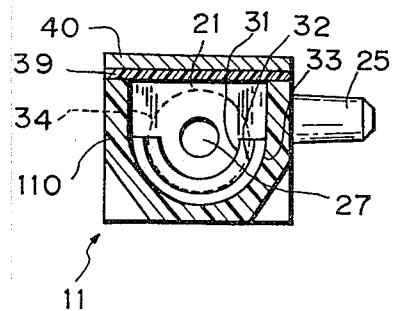
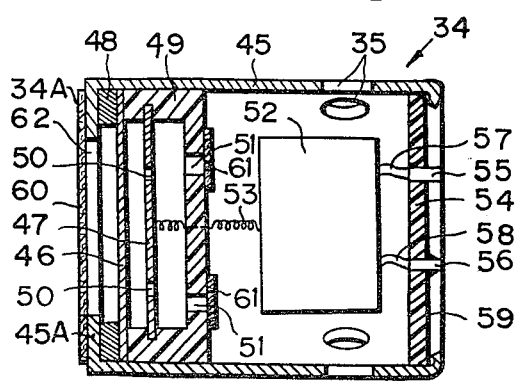

BLOOD PRESSURE MEASURING APPARATUS

BRIEF SUMMARY OF THE INVENTION

The present invention relates to a blood pressure measuring apparatus for measuring the systolic and diastolic blood pressures of a patient, and more particularly to an improved apparatus in which an electronic microphone for sensing Korotkoff sounds is disposed in a position remote from an occluding cuff.

A blood pressure measuring apparatus is well known which comprises an occluding cuff including an inflatable bladder, a squeezable bulb for applying air pressure to the bladder, a valve for reducing the pressure within the bladder, a microphone for sensing Korotkoff sounds, a pressure transducer for sensing the pressure within the bladder to generate pressure signals, and an electronic circuit device for determining the blood pressures of a patient. In this prior art apparatus, the microphone is disposed within the cuff so as to sense Korotkoff sounds generated from an artery of the patient. The microphone must be very accurately positioned over the artery so that its sound sensing surface may sense the Korotkoff sounds. This positioning work requires a fair amount of skill. Generally, the cuff includes two lines. One of the lines is an air pressure tubing connecting the bladder with the pressure transducer, and the other line is a cable establishing an electrical connection between the microphone and the electronic circuit device. The cuff must be wrapped and unwrapped for every blood pressure measurement, and the cable for the microphone then interferes with the handling of the cuff and, moreover, is easy to break.

It is, therefore, a primary object of the present invention to provide a blood pressure measuring apparatus comprising an occluding cuff and a measuring unit coupled to the cuff through a single air pressure tube.

It is a further object of the present invention to provide a blood pressure measuring apparatus which comprises a cuff including an inflatable bladder which acts also as a Korotkoff sound collector and, therefore, provides a larger Korotkoff sound sensing area than was the case with the prior art cuff including a built-in microphone which used to give the patient discomfort when the cuff was wrapped around his arm.

It is a still further object of the present invention to provide a blood pressure measuring apparatus comprising a microphone within a measuring unit, in which the bladder is inflated or deflated through an air pressure tube and the Korotkoff sounds collected by the bladder are propagated through said tube to the microphone.

It is another yet object of the present invention to provide a blood pressure measuring apparatus comprising an occluding cuff, a measuring unit and an air pressure tube connecting said cuff to said measuring unit and having a length such that its initial acoustical resonant frequency will be substantially equal to the frequency of Korotkoff sounds.

It is still another object of the present invention to provide a blood pressure measuring apparatus comprising a pressure-resistant microphone which is disposed in a pressurized air system of the apparatus.

Other objects and advantages of the present invention will be apparent upon reference to the following description in conjunction with accompanying drawings, in which:

BRIEF DESCRIPTION OF DRAWINGS

FIG. 3 is a sectional view showing the Korotkoff sound detection case which is employed in the apparatus of FIG. 1;

FIG. 4 is a sectional view taken along the line 4—4 of FIG. 3;

FIG. 5 is a sectional view taken along the line 5—5 of FIG. 3;

FIG. 6 is a sectional view of the microphone which is employed in the apparatus of FIG. 1.

DETAILED DESCRIPTION

Figure 1:
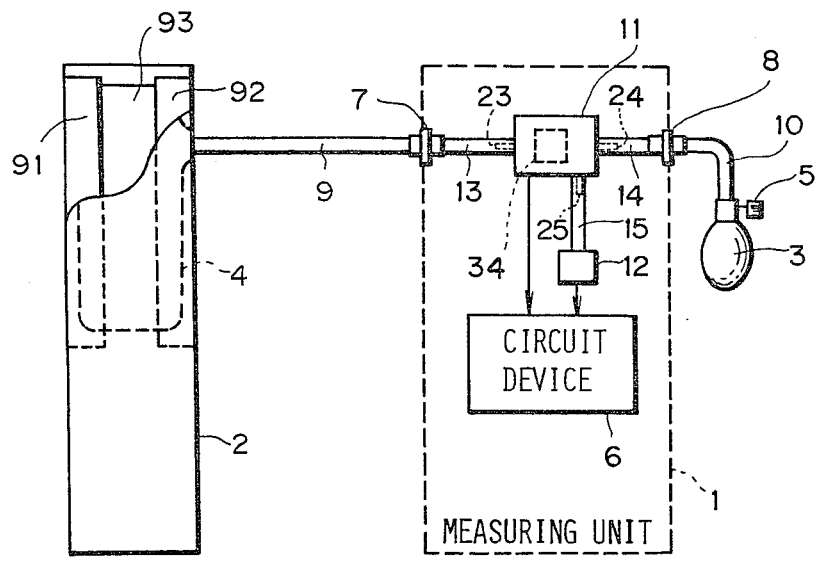
FIG. 1 is a schematic representation of a blood pressure measuring apparatus as a preferred embodiment of the present invention.

Referring now to FIG. 1, a blood pressure measuring apparatus as a preferred embodiment of the present invention comprises an occluding cuff 2 including an inflatable bladder 4; a measuring unit 1 including an electronic circuit device 6; a squeezable bulb 3; and air pressure tubes 9 and 10. The measuring unit 1 includes a pair of connectors 7 and 8 to which the tubes 9 and 10 are removably connected, respectively. The unit 1 further includes a Korotkoff sound detection case 11 enclosing a microphone 34; a pressure detector or transducer 12; and air tubes 13, 14 and 15. The case 11 includes a first connector 23 coupled to connector 7 via tube 13, a second connector 24 coupled to connector 8 via tube 14 and a third connector 25 coupled to pressure transducer 12 via tube 15. The case 11 includes a space through which air may flow from bulb 3 to bladder 4. The bulb 3 is provided with a bleeder valve 5 for bleeding air at a constant rate, for example, at a rate so as to reduce the pressure within bladder 4 by 3-4 mm of mercury per second. The bulb 3 and bleeder valve 5, taken together, constitute an air pressure control means. Thus, the bladder 4 is inflated by the bulb 3 through tube 10, case 11 and tubes 13 and 9 or deflated by the valve 5 via the reverse route. The transducer 12 senses pressures within bladder 4 and generates pressure signals for application to the circuit device 6. The microphone 34 senses Korotkoff sounds propagated from bladder 4 through tubes 9 and 13 and generates Korotkoff sound signals for application to circuit device 6.

The cuff 2 includes a pair of sound absorbing strips of sponge 91 and 92 as disposed on the surface of bladder 4 so as to absorb pulse sounds coming from an artery of the patient. As the cuff 2 is wrapped around the artery, the bladder 4 contacts the arm or other body portion of the patient through said strips 91 and 92 and the area 93 not covered by strips 91 and 92. The pulse sounds come from the heart of the patient and are substantially absorbed by the strip 91. As applied to the patient, the strip 92 on the distal side (remote from the heart) is provided for a better fitting of the cuff 2 on the patient's body, and may absorb a small portion of pulse sounds, although it may be omitted if desired.

Figure 2:
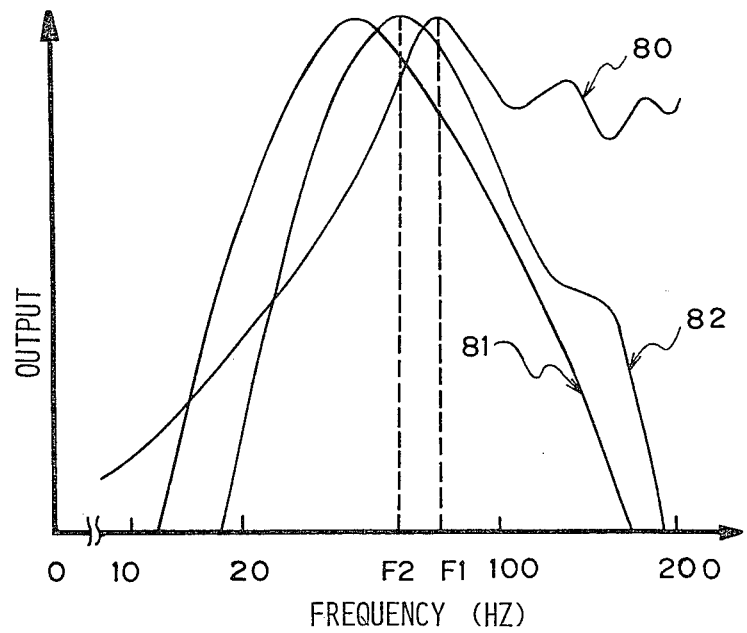
FIG. 2 is a graph showing frequency response curves of the air guiding passage, the band pass filter and the combined filter which are employed in the apparatus of FIG. 1.

The tubes 9, 13, 14 and 10 and case 11 constitute an air guiding passage which has definite acoustical resonant frequencies. In FIG. 2, there is shown an experimental frequency response curve 80 of the air guiding passage which has an initial resonant frequency F1. The circuit device 6 includes a band pass filter having a frequency response curve 81. The pulse sound signals (at below about 5 Hz) generated from microphone 34 are sharply blocked by the band pass filter. So, the combined filter composed of the air guiding passage and the band pass filter has a curve 82 with the largest gain at frequency F2 which is a Korotkoff sound frequency. Thus, the sounds collected by the bladder at area 93 are filtered by the combined filter having the curve 82 and the desired Korotkoff sounds are effectively extracted.

In FIGS. 3, 4 and 5, the Korotkoff sound detection case 11 is shown in detail. The case 11 is constructed in the shape of a box and has a space 21 for allowing air to flow freely therethrough. The case 11 consists of a metal cover plate 40 as an upper cover and a molded plastic cover 110 as a lower cover. The lower cover 110 has an opening which is closed by cover plate 40 through packing 39 as shown in FIG. 3. The cover 110 further includes on an inner wall a groove 32 for supporting microphone 34 and a groove 33 for allowing air to flow uniformly through holes 35 which are disposed in microphone 34. A pair of wires 37 for transmitting Korotkoff sound signals from microphone 34 to circuit device 6 extend outwardly through a pair of openings 36, which are sealed by caulking at 38. The microphone 34 is disposed within case 11 in such a manner that a sound sensing surface 34A of microphone 34 faces an air hole 26 bored in connector 23 so as to sense the Korotkoff sounds propagated therethrough.

As best shown in FIG. 6, the microphone 34 is a pressure-resistant condensor microphone. The microphone 34 comprises an external cylindrical metal housing 45, vibration electrode plate 46 and stationary electrode plate 47. The plates 46 and 47 are supported by an annular conductive ring 48 and an insulated ring frame 49 in a parallel relationship with each other. Namely, the peripheral edge of the plate 46 is sandwiched between rings 48 and 49. Within the housing 45, there is disposed an amplifier 52, the input terminal of which is connected to stationary plate 47 through wire 53. The amplifier 52 has output terminals which are connected to external terminals 55 and 56 through wires 57 and 58, respectively. The terminals 55 and 56 are fixed to a printed circuit board 54 which is supported by the housing 45. The board 54 includes a conductive pattern 59 which is connected between terminal 56 and conductive housing 45. Thus, the vibration plate 46 is electrically connected to terminal 56 through ring 48, housing 45 and pattern 59. The plate 47 and frame 49 have holes 50 and 51, respectively, and these holes 50 and 51, the holes 35 and an opening 62 of housing 45 serve to establish a uniform pressure throughout the housing 45. Nets 60 and 61 for preventing any foreign matter from entering into microphone 34 are disposed to cover the opening 62 and holes 51, respectively. The dimensions of the holes 51 and net 61 are designed to provide desired gains in the frequency range of Korotkoff sounds. It has been demonstrated that the smaller the effective acoustical diameter of holes 51 and net 61 is, the lower is the minimum sensible frequency of microphone 34. Thus, the microphone 34 has a stable frequency response characteristic independent of ambient pressure because the plate 46 is normally subject to the same atmospheric pressure at both front and back surfaces thereof. The microphone 34 has the maximum directional gain against the sounds impinging perpendicularly on the plate 46, viz. sensing surface 34A of FIG. 4.

Referring back to FIG. 4, as the bladder 4 is inflated by bulb 3, air flows along the solid arrow mark A, and as bladder 4 is deflated by valve 5, air flows, together with Korotkoff sounds, along the dotted arrow mark B so that the sounds are efficiently sensed by the microphone 34 at its sound sensing surface 34A. The bladder 4, case 11 and pressure transducer 12 are subject to uniform pressure. The circuit device 6 is designed to detect systolic and diastolic blood pressures in accordance with Korotkoff sound signals from microphone 34 and pressure signals from transducer 12.

Figure 7:
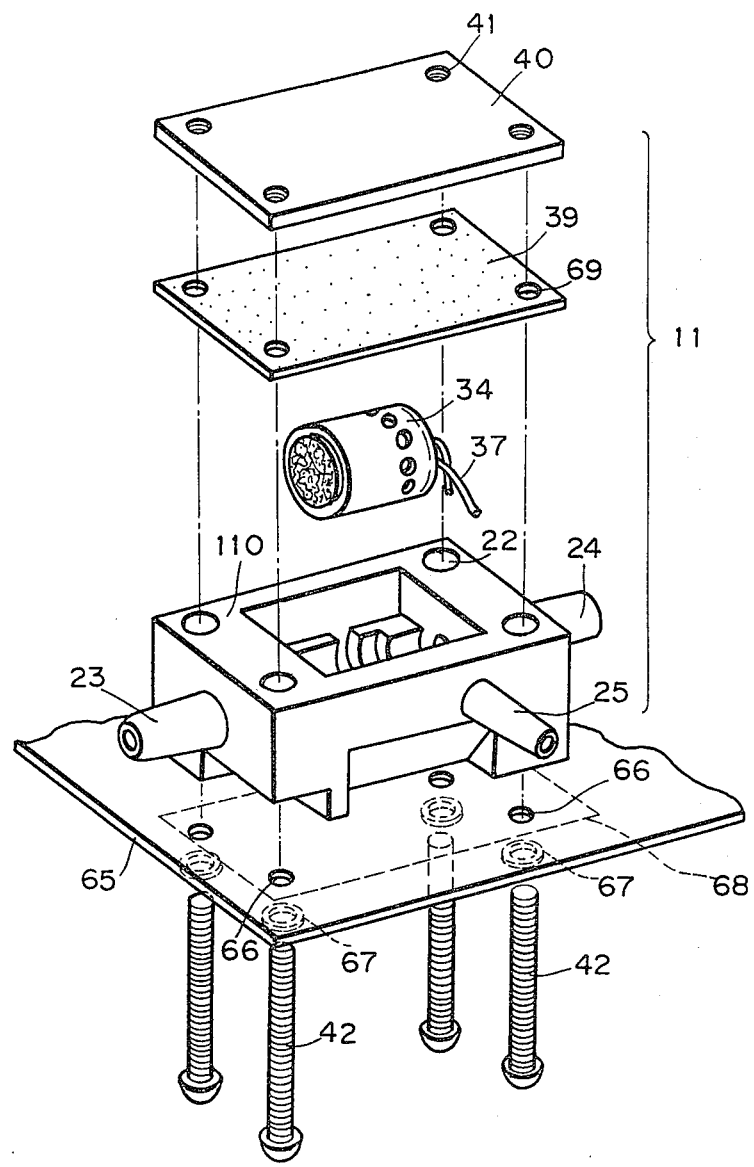
FIG. 7 is a perspective disassembled view showing the Korotkoff sound detection case mounted on the printed circuit board of the apparatus of FIG. 1.

Referring to FIG. 7, there is shown the Korotkoff sound detection case 11 as mounted on a printed circuit board 65 of the electronic circuit device 6 to provide a single component. The case 11 is fixed to the board 65 by means of four screws 42 and holes 41, 69, 22 and 66 which are respectively disposed in tapped plate 40, packing 39, cover 110 and board 65. On the bottom surface of the board 65, a ground pattern 68 is printed so that the plate 40 may be grounded through screws 42, and the case 11 may be substantially shielded from external noise, viz. the microphone 34 may be shielded.

In the present embodiment, the microphone is designed to have a single sound sensing surface, viz. unidirectional sound sensing surface. Alternatively, the Korotkoff sound detection case 11 may contain a bi-directional microphone, in which case the microphone equally senses Korotkoff sounds entering through air holes 26 and 27. In that case, the bulb 3 and cuff 2 may alternately be connected to the measuring unit 1. That is, the tube 10 may be connected to connector 7 and the tube 9 to connector 8. Thus, by switching the connections at the connectors 7 and 8, a patient who wants to measure his own blood pressures by himself may wrap the cuff 2 optionally around his left or right arm.

The above embodiment may be further modified. Instead of using the bulb 3 and valve 5 as pressure controlling means, an air pump for inflating or deflating the bladder 4 may be disposed within measuring unit 1, and the pump and Korotkoff sound detection case 11 may be constructed as a single unit without interposition of any connector therebetween.

According to the above embodiments, external sound noise is reduced in the blood pressure measuring apparatus, for as the inflatable bladder 4 is inflated, the pressure within bladder 4 becomes higher than the external pressure and the external sound noise cannot enter the bladder 4 due to its higher pressure. The microphone is disposed within the measuring unit, so that it may be protected from mechanical shock applied to the cuff on handling the cuff and the cuff may have a Korotkoff sound sensing area which is large and comfortable to the patient.

It should be understood that above description is merely illustrative of the present invention and that many changes and modifications may be made by those skilled in the art without departing from the scope of the appended claims.

What is claimed is:
1. Blood pressure measuring apparatus comprising an occluding cuff including an inflatable bladder, an air guiding passage one end of which is connected to said bladder,
air pressure control means connected to the other end of said passage for inflating or deflating said bladder through said passage, a microphone within said passage for sensing Korotkoff sounds which are propagated through said passage from said bladder and for generating Korotkoff sound signals, pressure transducer means for sensing the applied pressure within said bladder and for generating pressure signals, and circuit means operative in response to said Korotkoff sound and pressure signals to measure the systolic and diastolic blood pressures of a patient whose blood pressure is to be measured.

2. Blood pressure measuring apparatus according to claim 1, wherein said air guiding passage has a length such that the initial acoustical resonant frequency of the passage may be substantially equal to the frequency of said Korotkoff sounds.

3. Blood pressure measuring apparatus according to claim 1, wherein said circuit means includes a band pass filter designed so that the combined filter consisting of said band pass filter and the mechanical filter constituted by said passage may have a frequency pass band substantially equal to the frequency band of said Korotkoff sounds.

4. Blood pressure measuring apparatus according to claim 1 further comprising a case housing said microphone and having a space which serves as a portion of said passage.

5. Blood pressure measuring apparatus according to claim 4, wherein said case includes first and second connectors and said passage includes a tube connecting said bladder with said first connector and a tube connecting said second connector with said air pressure control means.

6. Blood pressure measuring apparatus according to claim 5, wherein said case further includes a third connector for connection to said pressure transducer means.

7. Blood pressure measuring apparatus according to claim 5, wherein said microphone is disposed within said case so that a sound sensing face thereof may face an air hole bored in said first connector.

8. Blood pressure measuring apparatus according to claim 4, wherein said circuit means includes a printed circuit board on which said case is mounted.

9. Blood pressure measuring apparatus according to claim 1, wherein said microphone includes a vibration electrode plate, a stationary electrode plate disposed in parallel thereto, and an external housing, said stationary electrode plate and external housing having holes for balancing the pressure in the microphone with the pressure in said passage.

10. Blood pressure measuring apparatus according to claim 1, wherein said cuff further includes sound absorbing strips on a predetermined area of said bladder.

11. Blood pressure measuring apparatus comprising
an occluding cuff including an inflatable bladder,
an air guiding passage one end of which is connected to said bladder,
air pressure control means connected to the other end of said passage for inflating or deflating said bladder through said passage,
a microphone within said passage for sensing Korotkoff sounds which are propagated through said passage from said bladder and for generating Korotkoff sound signals,
pressure transducer means for sensing the applied pressure within said bladder and for generating pressure signals and
circuit means operative in response to said Korotkoff sound and pressure signals to measure the systolic and diastolic blood pressures of a patient whose blood pressure is to be measured,
a case housing said microphone and having a space which serves as a portion of said passage,
said circuit means additionally including a printed circuit board on which said case is mounted,
said case additionally consisting of an upper cover made of metal and a lower cover made of insulation material;
said printed circuit board additionally including a conductive pattern corresponding to said lower cover, and
said upper cover and conductive pattern are grounded.

* * * * *